(12) United States Patent
Xu et al.

(10) Patent No.: US 9,283,190 B2
(45) Date of Patent: *Mar. 15, 2016

(54) HIGHLY EFFICIENT AND LONG-ACTING SLOW-RELEASE FORMULATION OF POORLY SOLUBLE DRUGS AND PREPARATION METHOD THEREOF

(75) Inventors: Ximing Xu, Jiangsu (CN); Jiangnan Yu, Jiangsu (CN); Yuan Zhu, Jiangsu (CN); Xia Cao, Jiangsu (CN)

(73) Assignee: JIANGSU UNIVERSITY (CN)

( * ) Notice: Subject to any disclaimer, the term of this patent is extended or adjusted under 35 U.S.C. 154(b) by 267 days.

This patent is subject to a terminal disclaimer.

(21) Appl. No.: 13/126,183

(22) PCT Filed: Nov. 23, 2009

(86) PCT No.: PCT/CN2009/001299
§ 371 (c)(1),
(2), (4) Date: Apr. 27, 2011

(87) PCT Pub. No.: WO2010/075664
PCT Pub. Date: Jul. 8, 2010

(65) Prior Publication Data
US 2011/0250269 A1 Oct. 13, 2011

(30) Foreign Application Priority Data
Dec. 31, 2008 (CN) .......................... 2008 1 0242994

(51) Int. Cl.
| | |
|---|---|
| *A61K 9/20* | (2006.01) |
| *A61K 31/357* | (2006.01) |
| *A61K 31/4422* | (2006.01) |
| *A61K 31/7048* | (2006.01) |
| *A61K 9/14* | (2006.01) |

(52) U.S. Cl.
CPC ............. *A61K 9/2054* (2013.01); *A61K 9/2077* (2013.01); *A61K 31/357* (2013.01); *A61K 31/4422* (2013.01); *A61K 31/7048* (2013.01); *A61K 9/143* (2013.01); *A61K 9/146* (2013.01)

(58) Field of Classification Search
CPC ..... A61K 9/2054; A61K 9/143; A61K 9/146; A61K 9/2077; A61K 31/357; A61K 31/4422; A61K 31/7048
See application file for complete search history.

(56) References Cited

U.S. PATENT DOCUMENTS

| | | | |
|---|---|---|---|
| 2011/0201680 A1* | 8/2011 | Xu et al. ........................ | 514/456 |
| 2012/0029064 A1* | 2/2012 | Xu et al. ........................ | 514/452 |

FOREIGN PATENT DOCUMENTS

| | | | | |
|---|---|---|---|---|
| CN | 200610096780 | * | 4/2008 | ........... A61K 31/357 |
| KR | WO2008/018716 | * | 2/2008 | ............... B01J 13/02 |
| WO | WO2009/078924 | * | 6/2009 | ............... A61K 9/16 |

OTHER PUBLICATIONS

Xu translation.*
C.R. Scholfield, Composition of Soybean Lecithin, 58 J Am. Oil Chem. Soc. 889, 1981).*
Zhu-Zhu Li, et al, Fabrication of Porous Silica Nanoparticles and Their Applications in Drug Release Control, 98 J Control Rel. 245 (2004).*
(I. Abarkan, et al, Tailored Macro/Microstructural Properties of Colloidal Silica Nanoparticles via Microemulsion Preparation, 25 Polyhedron 1763 (2006).*
N.M. Huang, et al, Single W/O Microemulsion Templating of CdS Nanoparticles, 39 J Mater. Sci. 2411 (2004).*
T. Heikkila, et al, Mesoporous Silica Material TUD-1 as a Drug Delivery System, 331 Intl. J Pharma. 113 (2007).*
Shi-Guo Zhu, et al, Poly(L-lysine)-Modified Silica Nanoparticles for the Delivery of antisense Oligonucleotides, 39 Biotechnol. Appl. Biochem. 179 (2004).*
Buckley, The Sol-Gel Preparation of Silica Gels, 71 J Chem. Edu. 599 (Jul. 1994).*
Zhang, Spherical Mesoporous Silica Nanoparticles for Loading and Release of the Poorly Water-soluble Drug Telmisartan, 145 J Control Rel. 257 (2010).*
Slowing, Mesoporous Silica Nanoparticles for Drug Delivery and Biosensing Applications, 17 Adv. Funct. Mater. 1225 (2007).*

* cited by examiner

*Primary Examiner* — Sean Basquill
(74) *Attorney, Agent, or Firm* — Schmeiser, Olsen & Watts, LLP

(57) ABSTRACT

A high-efficacy, long-acting, slow-release formulation of the poorly soluble drug, comprising solid dispersion of the poorly soluble drug, silica nanoparticles loaded with the poorly soluble drug, matrix material, and release enhancer, wherein the mass ratio of these components is solid dispersion of the poorly soluble drug: silica nanoparticles loaded with the poorly soluble drug: matrix material: release enhancer=1: 0.5~1.25: 0.1~0.3: 0.1~0.3; the said solid dispersion of the poorly soluble drug contains povidone K30, soybean lecithin, and acrylic resin IV, wherein the mass ratio of the drug and the accessory materials is poorly soluble drug: povidone K30: soybean lecithin: acrylic resin IV=1: 1~3: 0.3~0.8: 0.2~0.5. Compared with the existing formulations, the in vivo half life of the high-efficacy, long-acting formulation of the poorly soluble drug disclosed in this invention is 2.3~14.8 times longer while the mean residence time (MRT) of which is 7.94~4.52 times longer; when tested in vivo in Beagle dogs, this new formulation of the poorly soluble drug presents a smoother concentration-time curve and reaches a continuous release for 72 hours. This invention discloses its preparation method.

5 Claims, 2 Drawing Sheets

HIGHLY EFFICIENT AND LONG-ACTING SLOW-RELEASE FORMULATION OF POORLY SOLUBLE DRUGS AND PREPARATION METHOD THEREOF

FIELD OF THE INVENTION

This invention relates to a high-efficacy, long-acting, slow-release formulation of drugs and its preparation method, and particularly to a slow-release formulation and its preparation method that enable poorly soluble drugs to function 72 hours continuously in a slow-release mode and enhance its oral bioavailability.

BACKGROUND OF THE INVENTION 72-hour slow-release and higher oral bioavailability can be realized for the oral form of the poorly soluble drug insofar as such techniques as ordered mesoporous nanoparticles technique, hydrophilic gel matrix technique and solid dispersion technique are integrally adopted.

Due to its poor solubility in water, the poorly soluble drug is characteristic of being poorly absorbed by human body, fast rate of elimination, frequent occurrence of peak and trough phenomenon of the plasma concentration, low oral bioavailability, and hard to diversify its dosage form. Controlled release preparation of drugs is being widely used in virtue of its less total amount and frequency of administration, which consequently avoids peak and trough phenomenon of plasma concentration, reduces toxic and side effects and improves patients' adaptability [see: Lee K, Nguyen T, Hanley T, et, al. "Nanostructure of Liquid Crystalline Matrix Determines in vitro Sustained Release and in vivo Oral Absorption Kenetics for Hydrophilic Model Drugs." *International Journal of Pharmaceutics* 365.1-2 (2009):190.; Wang Jiexin, Wang Zhihui, Chen Jianfeng, et, al. "Direct Encapsulation of Water-soluble Drug into Silica Microcapsules for Sustained Release Applications." *Materials Research Bulletin* 43.12 (2008): 3374.]. Therefore, the defects such as great fluctuation of plasma concentration and frequent administrations of the poorly soluble drug can be effectively avoided when the drug is prepared in the controlled release form after having been solubilized. However, since the poorly soluble drug is not able to completely dissolve in water when being prepared in the controlled release form, an in advance solubilization is needed. The solubilized drug then can be used as the raw material for preparation of various forms of the slow-release drug. Techniques that can be utilized for solubilization of the poorly soluble drug include: solid dispersion technique, cyclodextrin inclusion technique, miceller solubilization technique and microemulsion technique [see: Shen Song, Xu Ximing, Yu Jiangnan. "Research Development on Solubilization of Poorly Water-soluble Drugs and Preparation of Its Controlled Release Forms." *Chinese Pharmaceutical Affairs* 21.3 (2007):196.; Guo Shengrong, Guo Li. "Effects of PVP K30 on Aqueous Solubility and Dissolution Properties of Daidzein." *Journal of Chinese Pharmaceutical Sciences* 13.1 (2004):42.; Z. Zuo, Y. K. Tam, J. Diakur, et, al. "Hydroxypropyl-beta-cyclidextrin-flutamide Inclusion Complex. II. Oral and Intravenous Pharmacokinetics of flutamide in the Rat." *J Pharm Sci* 5.3 (2002): 292.; C. M. Fernandes, M. T. Vieira, F. J. B. Veiga. "Physicochemical Characterization and in vitro Dissolution Behavior of Nicardipine-cyclodextrins Inclusion Compounds." *European Journal of Pharmaceutical Sciences* 15.1 (2002): 79.; Kang Moo Huh, Sang Cheon Lee, Yong Woo Cho. "Hydrotropic Polymer Micelle System for Delivery of Paclitaxel." *Journal of Controlled Release* 101.1-3 (2005): 59.].Compared with other said methods, solid dispersion technique is more extensively utilized in virtue of its simple preparation procedure and outstanding solubilization effect [see: Wei Zhenping, Mao Shirui, Bi Dianzhou, et, al. "Dissolution Improvement of Cisapride by Solid Dispersion with HPMC," *Journal of Chinese Pharmaceutical Science* 13.4 (2004):254.; Cui Fude, Yang Mingshi, Jiang Yanyan. "Design of Sustained-release Nitrendipine Microspheres Having Solid Dispersion Structure by Quasi-emulsion Solvent Diffusion Method." *Journal of Controlled Release* 97.3 (2003): 375.]. After having been solubilized, the poorly soluble drug can be either prepared in the conventional controlled release formulation or mixed with other controlled release materials at an appropriate ratio to prepare matrix type, osmotic pump type, or membrane-controlled type of formulations.

In recent years, much attention has been attracted to the special structure and features of the mesoporous material. It refers to a type of material containing multiple pores with diameter between 2 to 50 nanometers. A mesoporous material can be disordered or ordered according to the structure of the mesopores. The ordered mesoporous material enjoys the following structural characteristics: 1. long-range structure being ordered; 2. pore size distribution being narrow and adjustable between 1.5 to 10 nanometers; 3. specific surface area reaching as high as 1000 $m^2/g$; 4. high porosity and 5. rich unsaturated radicals on its surface. When used as a drug carrier, the ordered mesoporous material presents the following advantages: 1. being nontoxic, nonphysioactive and biocompatible; 2. having evenly distributed, adjustable pore canals, within which its rich silanic radicals act as active sites for combining organic guest molecules; the drug molecules, through combining with these radicals, distribute within the canals evenly as well. Since the drug is absorbed within the ordered mesoporous material, it acts in a slow-release way; 3. protecting the integrity of molecular structure of the drug. Therefore, an ideal controlled release can be achieved for the hydrophobic drug when the mesoporous material is adopted as the controlled release carrier. The release effect varies in relation to the structure of the pore canal of the ordered mesoporous material.

On the basis of "triple release" mechanism comprising quick-release of the solid dispersion, regular slow-release of the hydrophilic gel matrix and the long-acting, slow-release of the ordered mesoporous material, this invention discloses a new method for preparing the slow-release formulation of the poorly soluble drug that realizes 72-hour continuous release and enhances its oral bioavailability; the formulation prepared with this method simultaneously encompasses quick-release and double slow-release, and presents double pharmacokinetic advantages of high-efficacy and long-action.

DESCRIPTION OF THE INVENTION

Integrating solid dispersion technique, ordered mesoporous nanoparticles technique, and hydrophilic gel matrix technique together, this invention discloses a new method for preparing the slow-release formulation of the poorly soluble drug that realizes 72-hour continuous release and enhances its oral bioavailability; the formulation prepared with this method simultaneously encompasses quick-release and double slow-release, and presents double advantages of high-efficacy and long-action. Such poorly soluble drugs as silybinin, silymarin, nitrendipine and roxithromycin are taken as model drugs so that the beneficial effects of this high-efficacy, long-acting, slow-release formulation can be investigated.

The technical solution provided in this invention includes:

A high-efficacy, long-acting, slow-release formulation of the poorly soluble drug, comprising solid dispersion of the poorly soluble drug, silica nanoparticles loaded with the poorly soluble drug, slow-release matrix material, and release enhancer, wherein the mass ratio of these components is solid dispersion of the poorly soluble drug: silica nanoparticles loaded with the poorly soluble drug: matrix material: release enhancer=1: 0.5~1.25: 0.1~0.3: 0.1~0.3; the said solid dispersion of the poorly soluble drug contains povidone K30, soybean lecithin, and acrylic resin IV, wherein the mass ratio of the drug and the accessory materials is poorly soluble drug: povidone K30: soybean lecithin: acrylic resin IV=1: 1~3: 0.3~0.8: 0.2~0.5.

The said high-efficacy, long-acting, slow-release formulation of the poorly soluble drug is prepared in the form of tablets or capsules.

A method for preparing the said high-efficacy, long-acting slow-release formulation of the poorly soluble drug, comprising the following steps:

step 1. taking the poorly soluble drug 1 g, povidone K30 1-3 g, soybean lecithin 0.3-0.8 g and acrylic resin IV 0.2-0.5 g and injecting in absolute ethyl alcohol 20-40 ml (70° C. water-bath can be adopted to accelerate dissolution if necessary); after the said materials having dissolved, treating the solution with 60° C. water-bath; then rotarily evaporating the solution at 90 rpm till almost dry, and then treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion of the poorly soluble drug is therefore obtained and ready for later use;

step 2. taking cyclohexane 20-80 ml, adding in nonyl phenol 10(NP-10) 4-8 ml and mixing them together; adding in n-hexanol 1-3 ml, 25.6% ammonia water 1-3 ml and agitating for 1 hour at room temperature; slowly dropping in tetraethyl orthosilicate 3-5 ml and agitating for 24 hours at room temperature; adding in absolute ethyl alcohol 40-80 ml and treating with ultrasound for 1 hour; and then centrifugally separating at 15000 rpm for 15 min and washing the precipitate with distilled water three times; adding in some water, freezing and drying the substance in succession, and silica nanoparticles 8 g-32 g are therefore obtained;

taking the said silica nanoparticles 1 g, adding in 0.6 mol/L $Na_2CO_3$ solution 1000 ml, treating with ultrasound for 4-5 min under the condition of 60-70° C., 200 W, and then centrifugally separating at 15000 rpm and washing the precipitate with distilled water three times; adding in distilled water 10 ml, freezing and drying the substance in succession, and mesoporous silica nanoparticles are therefore obtained;

dissolving the poorly soluble drug 2 g in absolute ethyl alcohol 10-20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained;

step 3. taking solid dispersion of the poorly soluble drug 1 g, mixing it with hypromellose K4M 0.2-0.3 g and L-HPC 0.1-0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

step 4. taking solid dispersion of the poorly soluble drug 1.8 g, mixing it with hypromellose K4M 0.1-0.2 g, L-HPC 0.2-0.3 g and drug-loaded silica nanoparticles 1.25-2.5 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained;

step 5. mixing the slow-release granules 1 and the slow-release granules 2 at the ratio of 1:2.75~1:4; and then tabletting the mixed granules with the force around 40-60N; the high-efficacy, long-acting, slow-release tablet of the poorly soluble drug disclose in this invention is therefore obtained.

Adopting the said preparation method of the high-efficacy, long-acting, slow-release formulation of the poorly soluble drug, mixing the slow-release granules 1 prepared in step 3 and the slow-release granules 2 prepared in step 4 together at the ratio of 1:2.75~1:4; encapsulating the mixed granules and the high-efficacy, long-acting, slow-release capsule of the poorly soluble drug disclosed in this invention is obtained.

BENEFICIAL EFFECTS OF THE INVENTION:

1. This invention initiates a so-called "triple release" mechanism jointly realized by the quick-release of solid dispersion, the regular slow-release of hydrophilic gel matrix and the long-acting slow-release of mesoporous silica nanoparticles; based on the "double release" method comprising the quick-release technique and the regular slow-release technique, this mechanism fully utilizes the long-acting, slow-release characteristic of the drug-loaded ordered mesoporous material, an advantage resulting from its high absorption due to its high specific surface area and big pore volume; taking ordered mesoporous silica nanoparticles as carrier material and integrating solid dispersion technique, ordered mesoporous nanoparticles technique and hydrophilic gel matrix technique together, a new formulation of the poorly soluble drug that starts with quick-release, then regular slow-release, and long-acting slow-release at last is prepared, namely, the formulation encompasses quick-release and double slow-release simultaneously. Compared with the existing formulations through in vivo testing in Beagle dogs, the half life of the said high-efficacy, long-acting, slow-release formulation of the poorly soluble drug disclosed in this invention is 2.3~14.8 times longer while the mean residence time (MRT) of which is 7.94~4.52 times longer; the in vivo pharmacokinetic testing in Beagle dogs also indicates that this formulation of the poorly soluble drug presents a smoother concentration-time curve and reaches a continuous lease for 72 hours [see: FIG. 3 and FIG. 4].

2. This invention combines solid dispersion technique and nanotechnique together; on the one hand, soybean lecithin is added in during the preparation of the solid dispersion of the poorly soluble drug, which consequently enhances physical absorption of the poorly soluble drug; on the other hand, the utilization of nanoparticles prominently enhances the speed and extent of the physical absorption of the poorly soluble drug, which is contributive to higher bioavailability of the long-acting, slow-release formulation of the poorly soluble drug as well. Therefore, the formulation of the poorly soluble drug disclosed in this invention is not only a long-acting, slow-release one, but also a formulation of high-efficacy, that is to say, it is a formulation simultaneously presents the double advantages of high-efficacy and long-action. Compared with the control formulation through in vivo pharmacokinetic testing in Beagle dogs, the relative bioavailability of the long-acting, slow-release formulation of silybinin prepared with the method disclosed in this invention is 383%. In addition, the method disclosed in this invention can be utilized in developing sophisticated, high-efficacy and long-acting drug formulations that need to be administered only once three days.

3. Silica is biological compatible, nontoxic and extensively available; the silica nanoparticles prepared with the method disclosed in this invention have such advantages as simple preparation method, no requirement of special devices, fewer influencing factors during preparation, and higher repeatibility.

DETAILED DESCRIPTION OF PREFERRED EMBODIMENTS

Figure 1:
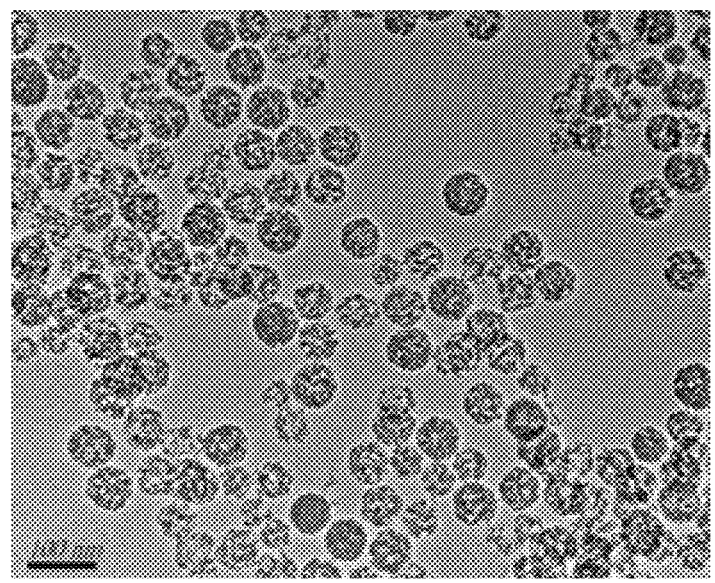
FIG. 1 is a TEM image of the mesoporous silica nanoparticles prepared in this invention.
Figure 2:
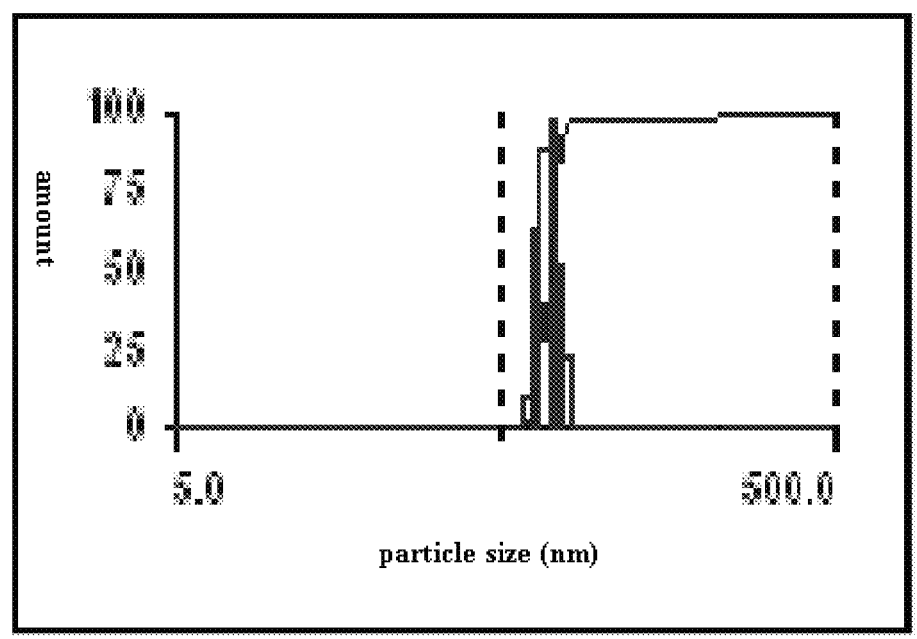
FIG. 2 is the particle size distribution graph of the mesoporous silica nanoparticles prepared in this invention.
Figure 3:
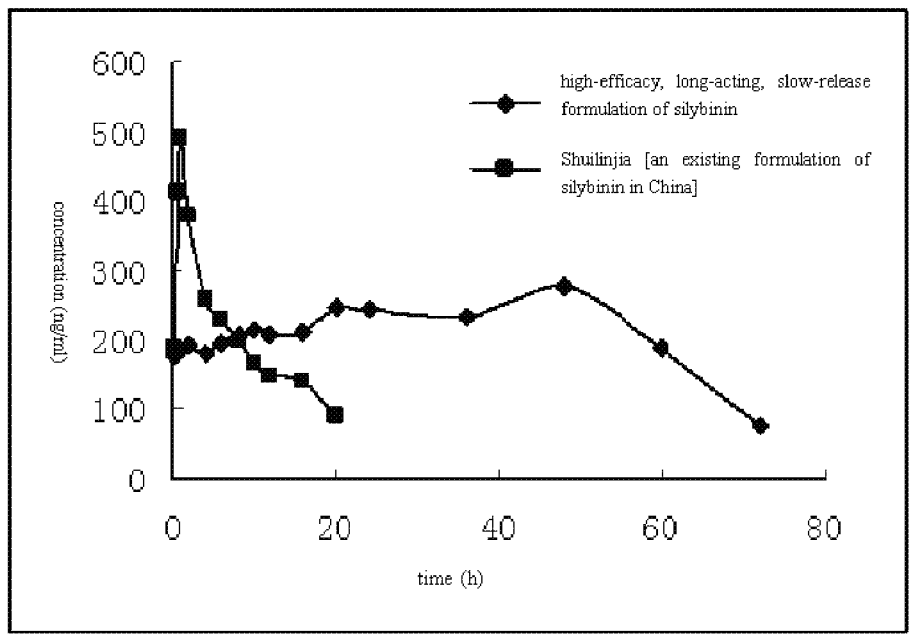
FIG. 3 is the concentration-time curve of the high-efficacy, long-acting, slow-release formulation of silybinin disclosed in this invention when tested in vivo in Beagle dogs.
Figure 4:
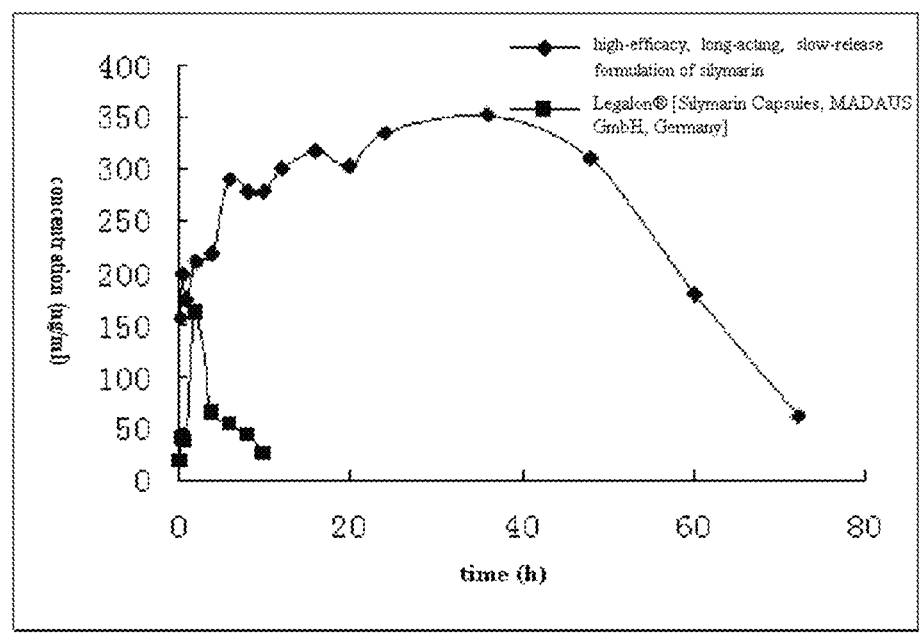
FIG. 4 is the concentration-time curve of the high-efficacy, long-acting, slow-release formulation of silymarin disclosed in this invention when tested in vivo in Beagle dogs.

The materials and devices required for the following embodiments include:

experiment materials: povidone K30 (Shanghai Shengpu New Materials Co., Ltd.); soybean lecithin (Shanghai Taiwei Pharmaceutical Co., Ltd.); acrylic resin IV (Huainan Shanhe Medical Accessories Co., Ltd.); tetraethyl orthosilicate (Chemical Reagent Co., Ltd. of China National Pharmaceutical Group); hypromellose K4M (Shanghai Colorcon Coating Technology Co., Ltd.); L-HPC (Shanghai Colorcon Coating Technology Co., Ltd);

experiment devices: rotary evaporator (Heidolph, Germany); H66025 ultrasonic cleaner (Wuxi Ultrasonic Devices Factory); ADP single punch tablet machine (Shanghai Tianxiang Jiantai Pharmaceutical machinery Co., Ltd.).

Embodiment I

Taking silymarin 1 g, povidone K30 1 g, soybean lecithin 0.2 g and acrylic resin IV 0.1 g and injecting in absolute ethyl alcohol 20 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 30 ml, adding in nonyl phenol 10(NP-10) 4 ml and mixing them together; adding in n-hexanol 1 ml, 25.6% ammonia water 1 ml and agitating for 1 hour at room temperature; slowly dropping in tetraethyl orthosilicate 3 ml and agitating for 24 hours at room temperature; adding in absolute ethyl alcohol 40 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 2 g, adding in 0.6 mol/L Na$_2$CO$_3$ solution 3000 ml, treating with ultrasound for 4' 20", 4' 10" and 4' under the condition of 60° C. 200 W, 65° C. 200 W and 70° C. 200 W respectively, and then centrifugally separating at 15000 rpm for 15 min and washing the precipitate with distilled water three times; adding in distilled water 1 ml, freezing and drying the substance in succession, and mesoporous silica nanoparticles are therefore obtained.

Dissolving silybinin 3 g in absolute ethyl alcohol 20 ml, soaking mesoporous silica nanoparticles 1.5 g in the solution for 24 hours, and then centrifugally separating at 15000 rpm for 15 min and washing the precipitate with absolute ethyl alcohol three times; adding in distilled water 1 ml, freezing and drying the substance in succession, and drug-loaded nanoparticles are therefore obtained.

Taking silybinin solid dispersion 1 g, mixing it with hypromellose K4M 0.2 g and L-HPC 0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silybinin solid dispersion 1.8 g, mixing it with hypromellose K4M 0.36 g, L-HPC 0.4 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:2; and then tableting the mixed granules with the force around 40-60N; the high-efficacy, long-acting, slow-release tablet of silybinin is therefore obtained.

Embodiment II

Taking silybinin 1 g, povidone K30 3 g, soybean lecithin 0.8 g and acrylic resin IV 0.5 g and injecting in absolute ethyl alcohol 40 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the silybinin solid dispersion is therefore obtained and ready for later use.

Taking cyclohexane 80 ml, adding in nonyl phenol 10(NP-10) 8 ml and mixing them together; adding in n-hexanol 3 ml, 25.6% ammonia water 3 ml and agitating for 1 hour at room temperature; slowly dropping in tetraethyl orthosilicate 5 ml and agitating for 24 hours at room temperature; adding in absolute ethyl alcohol 80 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 3 g, adding in 0.6 mol/L Na$_2$CO$_3$ solution 3000 ml, treating with ultrasound for 4' 20", 4' 10" and 4' under the condition of 60° C. 200 W, 65° C. 200 W and 70° C. 200 W respectively, and then centrifugally separating at 15000 rpm for 15 min and washing the precipitate with distilled water three times; adding in distilled water 1 ml, freezing and drying the substance in succession, and mesoporous silica nanoparticles are therefore obtained.

Dissolving silybinin 3 g in absolute ethyl alcohol 20 ml, soaking mesoporous silica nanoparticles 1.5 g in the solution for 24 hours, and then centrifugally separating at 15000 rpm for 15 min and washing the precipitate with absolute ethyl alcohol three times; adding in distilled water 1 ml, freezing and drying the substance in succession, and drug-loaded nanoparticles are therefore obtained.

Taking silybinin solid dispersion 1.8 g, mixing it with hypromellose K4M 0.4 g and L-HPC 0.4 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained. Taking silybinin solid dispersion 1.8 g, mixing it with hypromellose K4M 0.36 g, L-HPC 0.4 g and drug-loaded silica nanoparticles 3 g, and then adding in some 70% syrup so that a certain soft substance is obtained; sieving the soft substance with 16 mesh and the wet granules so obtained are baked at 60° C. for 30min, reshaping the granules with 16 mesh and the slow-release granules 2 are therefore obtained.

Mixing the slow-release granules 1 and the slow-release granules 2 at the ratio of 2:3; and then encapsulating the mixed granules so that the high-efficacy, long-acting, slow-release capsule of silybinin is obtained.

Embodiment III

Taking silymarin 1 g, povidone K30 1.2 g, soybean lecithin 0.4 g and acrylic resin IV 0.3 g and injecting in absolute ethyl alcohol 25 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the silybinin solid dispersion is therefore obtained and ready for later use.

Taking cyclohexane 30 ml, adding in nonyl phenol 10(NP-10) 5 ml and mixing them together; adding in n-hexanol 1.2 ml, 25.6% ammonia water 1.5 ml and agitating for 1 hour at room temperature; slowly dropping in tetraethyl orthosilicate 3.5 ml and agitating for 24 hours at room temperature; adding in absolute ethyl alcohol 50 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 1 g, adding in 0.6 mol/L $Na_2CO_3$ solution 1000 ml, treating with ultrasound for 45 min under the condition of 65° C., 200 W, and then centrifugally separating at 15000 rpm for 15 min and washing the precipitate with distilled water three times; adding in distilled water 10 ml, freezing and drying the substance in succession, and mesoporous silica nanoparticles are therefore obtained.

Dissolving silymarin 2 g in absolute ethyl alcohol 20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained.

Taking silymarin solid dispersion 1 g, mixing it with hypromellose K4M 0.2 g and L-HPC 0.2 g, and then adding in some 70% syrup so that a certain soft substance is obtained; sieving the soft substance with 16 mesh and the wet granules so obtained are baked at 60☐ for 30 min, reshaping the granules with 16 mesh and the slow-release granules 1 are therefore obtained.

Taking silymarin solid dispersion 1 g, mixing it with hypromellose K4M 0.1 g, L-HPC 0.3 g and drug-loaded silica nanoparticles 2 g, and then adding in some 70% syrup so that a certain soft substance is obtained; sieving the soft substance with 16 mesh and the wet granules so obtained are baked at 60☐ for 30 min, reshaping the granules with 16 mesh and the slow-release granules 2 are therefore obtained.

Mixing the slow-release granules 1 and the slow-release granules 2 at the ratio of 2:3; and then tableting the mixed granules with the force around 40-60N; the high-efficacy, long-acting, slow-release tablet of silymarin is therefore obtained.

Embodiment IV

Taking silymarin 1 g, povidone K30 1.5 g, soybean lecithin 0.5 g and acrylic resin IV 0.4 g and injecting in absolute ethyl alcohol 30 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the silybinin solid dispersion is therefore obtained and ready for later use.

Taking cyclohexane 50 ml, adding in nonyl phenol 10(NP-10) 6 ml and mixing them together; adding in n-hexanol 2.2 ml, 25.6% ammonia water 1.8 ml and agitating for 1 hour at room temperature; slowly dropping in tetraethyl orthosilicate 4.2 ml and agitating for 24 hours at room temperature; adding in absolute ethyl alcohol 60 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 1 g, adding in 0.6 mol/L $Na_2CO_3$ solution 1000 ml, treating with ultrasound for 45 min under the condition of 65° C., 200 W, and then centrifugally separating at 15000 rpm for 15 min and washing the precipitate with distilled water three times; adding in distilled water 10 ml, freezing and drying the substance in succession, and mesoporous silica nanoparticles are therefore obtained.

Dissolving silymarin 2 g in absolute ethyl alcohol 20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained.

Taking silymarin solid dispersion 1 g, mixing it with hypromellose K4M 0.22 g and L-HPC 0.22 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silymarin solid dispersion 1 g, mixing it with hypromellose K4M 0.15 g, L-HPC 0.25 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 2:3; and then encapsulating the mixed granules so that the high-efficacy, long-acting, slow-release capsule of silymarin is obtained.

Embodiment V

Taking roxithromycin 1 g, povidone K30 2 g, soybean lecithin 0.5 g and acrylic resin IV 0.3 g and injecting in absolute ethyl alcohol 30 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the roxithromycin solid dispersion is therefore obtained and ready for later use.

Taking cyclohexane 70 ml, adding in nonyl phenol 10(NP-10) 6 ml and mixing them together; adding in n-hexanol 1 ml, 25.6% ammonia water 1.5 ml and agitating for 1 hour at room temperature; slowly dropping in tetraethyl orthosilicate 6 ml and agitating for 24 hours at room temperature; adding in absolute ethyl alcohol 60 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 2 g, adding in 0.6 mol/L $Na_2CO_3$ solution 2000 ml, treating with ultrasound for 45 min under the condition of 70° C., 200 W, and then centrifugally separating at 15000 rpm for 15 min and washing the precipitate with distilled water three times; adding in distilled water 10 ml, freezing and drying the substance in succession, and mesoporous silica nanoparticles are therefore obtained.

Dissolving roxithromycin 2 g in absolute ethyl alcohol 15 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained.

Taking roxithromycin solid dispersion 1.4 g, mixing it with hypromellose K4M 0.5 g and L-HPC 0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained. Taking roxithromycin solid dispersion 2.1 g, mixing it with hypromellose K4M 0.4 g, L-HPC 0.4 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:1; and then tableting the mixed granules with the force around 40-60N; the high-efficacy, long-acting, slow-release tablet of roxithromycin is therefore obtained.

Embodiment VI

Taking nitrendipine 1 g, povidone K30 1.8 g, soybean lecithin 0.6 g and acrylic resin IV 0.2 g and injecting in absolute ethyl alcohol 30 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the nitrendipine solid dispersion is therefore obtained and ready for later use.

Taking cyclohexane 60 ml, adding in nonyl phenol 10(NP-10) 5 ml and mixing them together; adding in n-hexanol 1 ml, 25.6% ammonia water 1.5 ml and agitating for 1 hour at room temperature; slowly dropping in tetraethyl orthosilicate 5.5 ml and agitating for 24 hours at room temperature; adding in absolute ethyl alcohol 70 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 2 g, adding in 0.6 mol/L $Na_2CO_3$ solution 3000 ml, treating with ultrasound for 4' 20", 4' 10" and 4' under the condition of 60° C. 200 W, 65° C. 200 W and 70° C. 200 W respectively, and then centrifugally separating at 15000 rpm and washing the precipitate with distilled water three times; adding in distilled water 1 ml, freezing and drying the substance in succession, and mesoporous silica nanoparticles are therefore obtained.

Dissolving nitrendipine 2 g in absolute ethyl alcohol 15 ml, soaking mesoporous silica nanoparticles 1 g in the solution for 24 hours, and then centrifugally separating at 15000 rpm for 15 min and washing the precipitate with absolute ethyl alcohol three times; adding in distilled water 1 ml, freezing and drying the substance in succession, and drug-loaded nanoparticles are therefore obtained.

Taking nitrendipine solid dispersion 1.4 g, mixing it with hypromellose K4M 0.5 g and L-HPC 0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking nitrendipine solid dispersion 2.1 g, mixing it with hypromellose K4M 0.4 g, L-HPC 0.3 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:1; and then tableting the mixed granules with the force around 40-60N; the high-efficacy, long-acting, slow-release tablet of nitrendipine is therefore obtained.

What is claimed is:

1. A method for preparing a high-efficacy, long-acting slow-release formulation of the poorly soluble drug, comprising the following steps:

step 1. taking the poorly soluble drug 1 g, povidone K30 1-3 g, soybean lecithin 0.3-0.8 g and acrylic resin IV 0.2-0.5 g and injecting in absolute ethyl alcohol 20-40 ml (70° C. water-bath can be adopted to accelerate dissolution if necessary); after the said materials having dissolved, treating the solution with 60° C. water-bath; then rotarily evaporating the solution at 90 rpm, and then treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion of the poorly soluble drug is therefore obtained and ready for later use;

step 2. taking cyclohexane 20-80 ml, nonyl phenol 10(NP-10) 4-8 ml and mixing them together; adding in-n-hexanol 1-3 ml, 25.6% ammonia water 1-3 ml and agitating for 1 hour at room temperature; slowly dropping in tetraethyl orthosilicate 3-5 ml and agitating for 24 hours at room temperature; adding in absolute ethyl alcohol 40-80 ml and-treating with ultrasound for 1 hour; and then centrifugally separating at 15000 rpm for 15 min and washing the precipitate with distilled water three times; adding water, freezing and drying the substance in succession, and silica nanoparticles 8 g-32 g are therefore obtained;

taking the said silica nanoparticles 1 g, adding in 0.6 mol/L $Na_2CO_3$ solution 1000 ml, treating with ultrasound for 4-5 min under the condition of 60-70° C., 200 W, and then centrifugally separating at 15000 rpm for 15 min; and washing the precipitate with distilled water three times; adding in distilled water 10 ml, freezing and drying the substance in succession, and mesoporous silica nanoparticles are therefore obtained;

dissolving the poorly soluble drug 2 g in absolute ethyl alcohol 10-20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained;

step 3. taking solid dispersion of the poorly soluble drug 1 g, mixing it with hypromellose K4M 0.2-0.3 g and L-HPC 0.1-0.2 g, sieving with 16 mesh and the wet granules so obtained are baked at 60° C. for 30 min, reshaping the granules with 16 mesh and the slow-release granules 1 are therefore obtained;

step 4. taking solid dispersion of the poorly soluble drug 1.8 g, mixing it with hypromellose K4M 0.1-0.2 g, L-HPC 0.2-0.3 g and drug-loaded silica nanoparticles 1.25-2.5 g; sieving with 16 mesh and the wet granules so obtained are baked at 60° C. for 30 min, reshaping the granules with 16-mesh and the slow-release granules 2 are therefore obtained;

step 5. mixing the slow-release granules 1 and the slow-release granules 2 at the ratio of 1:2.75~1:4; and-then tableting the mixed granules with the force around 40-60N; the high-efficacy, long-acting, slow-release tablet of the poorly soluble drug disclose in this invention is therefore obtained.

2. A method for preparing for the high-efficacy, long-acting, slow-release formulation of the poorly soluble drug as is defined in claim 1, wherein the slow-release granules 1 prepared in step 3 and the slow-release granules 2 prepared in step 4 are mixed at the ratio of 1:2.75~1:4, and then are encapsulated together to form the high-efficacy, long-acting, slow-release capsule of the poorly soluble drug.

3. A method for preparing a high-efficacy, long-acting slow-release formulation of a poorly soluble drug, comprising the following steps:

providing a solid dispersion of the poorly soluble drug;
preparing a mixture of cyclohexane, nonyl phenol 10(NP-10), n-hexanol and 25.6% ammonia water;
slowly dropping in tetraethyl orthosilicate directly into the mixture;
adding absolute ethyl alcohol to the mixture;
treating the mixture with ultrasound and then centrifugally separating at 15000 rpm;
washing a precipitate of the mixture with distilled water, forming a solution;
adding water, freezing and drying the solution in succession to obtain silica nanoparticles;
adding a $Na_2CO_3$ solution to the silica nanoparticles forming a silica nanoparticle solution;
treating the silica nanoparticle solution with ultrasound followed by centrifugally separating a precipitate of the silica nanoparticle solution at 15000 rpm;
washing the precipitate of the silica nanoparticle solution with distilled water three times; adding distilled water to the precipitate of the silica nanoparticle solution, forming a precipitate solution;
freezing and drying the precipitate solution in succession to obtain mesoporous silica nanoparticles with a porous diameter between 2-50 nm;
dissolving the poorly soluble drug in absolute ethyl alcohol, forming an absolute ethyl alcohol solution;
soaking the mesoporous silica nanoparticles in the absolute ethyl alcohol solution;
centrifugally separating the mesoporus silica nanoparticle in the absolute ethyl alcohol solution at 15000 rpm;
freezing and drying the absolute ethyl alcohol solution in succession to obtain drug-loaded silica nanoparticles;
mixing a first portion of the solid dispersion with hypromellose K4M and low-substituted hydroxypropyl cellulose (L-HPC);
sieving the mixture of the first portion of the solid dispersion with hypromellose K4M and low-substituted hydroxypropyl cellulose (L-HPC) into a first set of granules;
baking the first set granules;
reshaping the first set of granules with 16 mesh to obtain a first set of slow-release granules;
mixing a second portion of the solid dispersion with hypromellose K4M, low-substituted hydroxypropyl cellulose (L-HPC) and drug-loaded silica nanoparticles;
sieving the mixture of the second portion of the solid dispersion with hypromellose K4M, low-substituted hydroxypropyl cellulose (L-HPC) and drug-loaded silica nanoparticles into a second set of granules;
baking the second set of granules;
reshaping the second set of granules with 16 mesh to obtain a second set of slow-release granules; and
mixing the first set of slow-release granules and the second set of slow-release granules together at the ratio of 1:2.75~1:4.

4. The method of claim 3, further comprising the additional step of tableting the mixture of the first set of slow-release granules and the second set of slow-release granules.

5. The method as is defined in claim 3, further comprising the step of encapsulating the mixture of the first set of slow-release granules and the second set of slow-release granules in a capsule.

* * * * *